(12) United States Patent
Smits

(10) Patent No.: US 9,975,823 B2
(45) Date of Patent: May 22, 2018

(54) PROCESS FOR THE PREPARATION OF 5-BROMO-1,2,3-TRICHLOROBENZENE

(71) Applicant: SYNGENTA PARTICIPATIONS AG, Basel (CH)

(72) Inventor: Helmars Smits, Stein (CH)

(73) Assignee: Syngenta Participations AG, Basel (CH)

( * ) Notice: Subject to any disclaimer, the term of this patent is extended or adjusted under 35 U.S.C. 154(b) by 0 days. days.

(21) Appl. No.: 15/515,322

(22) PCT Filed: Oct. 8, 2015

(86) PCT No.: PCT/EP2015/073219
§ 371 (c)(1),
(2) Date: Mar. 29, 2017

(87) PCT Pub. No.: WO2016/058897
PCT Pub. Date: Apr. 21, 2016

(65) Prior Publication Data
US 2017/0267611 A1  Sep. 21, 2017

(30) Foreign Application Priority Data
Oct. 14, 2014 (EP) ..................................... 14188742

(51) Int. Cl.
| | | |
|---|---|---|
| *C07C 17/04* | (2006.01) | |
| *C07C 17/06* | (2006.01) | |
| *C07C 17/12* | (2006.01) | |
| *C07C 17/35* | (2006.01) | |
| *C07C 17/358* | (2006.01) | |
| *C07C 25/10* | (2006.01) | |

(52) U.S. Cl.
CPC .............. *C07C 17/04* (2013.01); *C07C 17/06* (2013.01); *C07C 17/12* (2013.01); *C07C 17/35* (2013.01); *C07C 17/358* (2013.01); *C07C 25/10* (2013.01)

(58) Field of Classification Search
CPC .................................................... C07C 17/358
See application file for complete search history.

(56) References Cited

U.S. PATENT DOCUMENTS 4,347,390 A * 8/1982 Nishiyama ............... C07C 17/12
570/202
5,792,892 A * 8/1998 Hagemann ............... C07B 39/00
562/493

OTHER PUBLICATIONS

Rajesh, K. et al. "Bromination of Deactivated Aromatics: A Simple and Efficient Method" J. Org. Chem. 2007, 72, 5867-5869 (Year: 2007).*

Tanemura, K. et al. "Halogenation of Aromatic Compounds by N-chloro-, N-bromo-, and N-iodosuccinimide" Chemistry Letters vol. .32, No. 10 (2003) (Year: 2003).*
International Search Report for PCT/EP2015/073219, dated Nov. 26, 2015.
Schnürch, Michael et al: "Halogen-Dance Reactions—A Review", Chemical Society Reviews, Chemical Society, London, GB, vol. 36, Jan. 1, 2007 {Jan. 1, 2007), pp. 1046-1057, XP002636262, ISSN: 0306-0012, DOI: 10.1039/B607701N.
Heiss, Christophe et al: "Promoting or Preventing Haloaryllithium Isomerizations: Differential Basicities and Solvent Effects as the Crucial Variables". Synthesis. vol. 2005. No. 04, Jan. 1, 2005 (Jan. 1, 2005). pp. 617-621. XP055169944. ISSN: 0039-7881. DOI: 10.1055/s-2005-861787.
Mach, Martin H. et al: "Participation of oligochlorobenzenes in the base-catalyzed halogen dance". The Journal of Organic Chemistry. vol. 45. No. 23., Nov. 1, 1980 (Nov. 1, 1980). pp. 4660-4666. XP055169941. ISSN: 0022-3263. DOI: 10.1021 jjo01311a022.

(Continued)

*Primary Examiner* — Medhanit W Bahta
(74) *Attorney, Agent, or Firm* — James Cueva

(57) ABSTRACT

The present invention relates to a process for the preparation of a compound of formula I (I), comprising reacting a compound of formula II (II), with a brominating agent in the presence of an acidic catalyst to a compound of formula III (III), and reacting the compound of formula III in tetrahydrofuran or 2-methyl-tetrahydrofuran with potassium tert-butoxide to a compound of formula I.

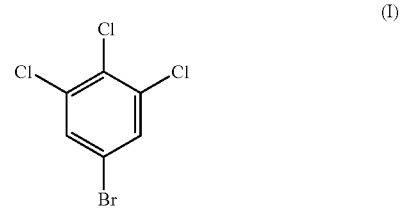

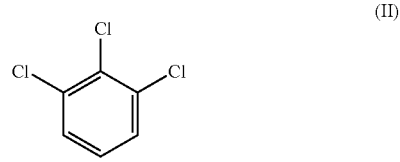

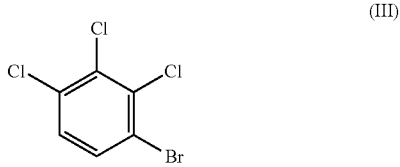

4 Claims, No Drawings

(56) References Cited

OTHER PUBLICATIONS

Sott et al: "Synthesis of dioxin-like monofluorinated PCBs: for the use as internal standards for PCB analysis". Tetrahedron. Elsevier Science Publishers. Amsterdam. NL. vol. 64. No. 18. Jan. 5, 2008 (Jan. 5, 2008). pp. 4135-4142. XP022551930. ISSN: 0040-4020. DOI: 10.1016/J.TET.2008.01.003.
Schlosser, Manfred et al: "Proton Mobility in 2-Substituted 1, 3-Dichlorobenzenes: "ortho" or "meta" Metalation?". European Journal of Organic Chemistry. vol. 2006. No. 19. Oct. 1, 2006 (Oct. 1, 2006). pp. 4398-4404, XP055170008. ISSN: 1434-193X. DOI: 10.1002jejoc.200600350 p. 4401.
Extended European Search Report for EP14188742.2, dated Feb. 25, 2015.

\* cited by examiner

PROCESS FOR THE PREPARATION OF 5-BROMO-1,2,3-TRICHLOROBENZENE

RELATED APPLICATION INFORMATION

This application is a 371 of International Application No. PCT/EP2015/073219 filed Oct. 8, 2015, which claims priority to EP Application No. 14188742.2, filed Oct. 14, 2014, the contents of which are incorporated by reference herein.

The present invention relates to the preparation of 1,2,3-trichloro-5-bromo-benzene using 1-bromo-2,3,4-trichloro benzene as an intermediate.

1,2,3-trichloro-5-bromo benzene is an important intermediate for the preparation of biologically active compounds in both pharmaceutical and agrochemical industries as for example described in WO 2012/120135.

According to Narander, N.; Srinivasu, P.; Kulkarni, S. J.; Raghavan, K. V. Synth. Comm. 2000, 30, 3669 and Sott, R.; Hawner, C.; Johansen, J. E. Tetrahedron 2008, 64, 4135. 5-bromo-1,2,3-trichloro-benzene can be prepared according to the following Scheme 1:

Scheme 1:

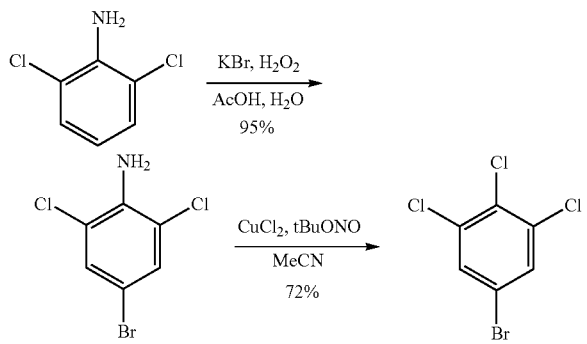

A significant disadvantage of the known process is the need to use a stoichiometric amount of copper chloride in the second step thus making the process environmentally unfavorable on a large scale. The other problematic issue is the formation of significant amounts of byproducts in the second step, most notably of 1-bromo-3,5-dichloro-benzene.

It was found that 1,2,3-trichloro-5-bromo-benzene can be advantageously prepared by using 1-bromo-2,3,4-trichloro benzene as an intermediate. It is therefore the object of the present invention to provide a process for the preparation of 1,2,3-trichloro-5-bromo benzene using 1-bromo-2,3,4-trichloro benzene as an intermediate. This process shows a favorable environmental profile, high yields and low amounts of byproducts.

Base-induced movement of a halogen atom from one position to another in an aromatic ring is called a halogen dance reaction and is known in both aromatic and heteroaromatic systems provided that there is a significant difference in acidity of ring hydrogens (review article: Schnürch, M.; Spina, M.; Khan, A. F.; Mihovilovic, M. D.; Stanetty, P. Chem. Soc. Rev. 2007, 36, 1046). However, in the case of simple aromatic systems, the reaction is rarely of synthetic value due to low selectivity and significant formation of byproducts arising from formation of benzyne intermediates (for example as described in: Mach, M. H.; Bunnett, J. F. J. Org. Chem. 1980, 45, 4660). In the few synthetically useful examples, low temperature in combination with very strong bases were required for obtaining good yields, for example as described in Heiss, C.; Rausis, T.; Schlosser, M. Synthesis 2005, 4, 617 (Scheme 2):

Scheme 2

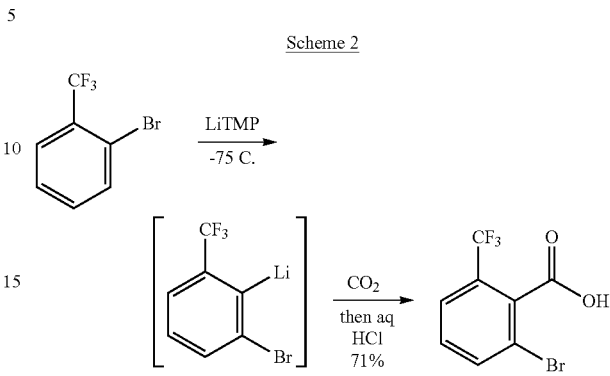

It was surprisingly found that 1-bromo-2,3,4-trichloro-benzene could be isomerized to 1,2,3-trichloro-5-bromo-benzene using catalytic amounts of potassium tert-butoxide in tetrahydrofuran or 2-methyl-tetrahydrofuran at ambient temperature. Under these conditions, approximately 80:20 equilibrium ratio between 1,2,3-trichloro-5-bromo-benzene and 1-bromo-2,3,4-trichloro-benzene are reached. However this doesn't result in loss of material since the starting material can be separated and recycled.

Thus, according to this invention, there is provided a process for the preparation of a compound of formula I

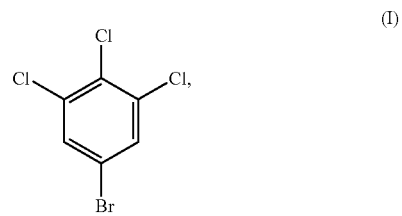

(I)

comprising
a) reacting a compound of formula II

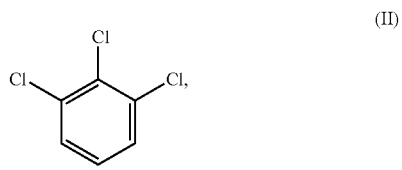

(II)

with a brominating agent in the presence of an acidic catalyst to a compound of formula III,

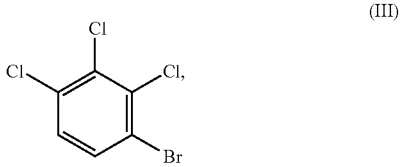

(III)

and b) reacting the compound of formula III in tetrahydrofuran or 2-methyl-tetrahydrofuran with potassium tert-butoxide to a compound of formula I.

The following scheme 3 describes the reactions of the invention in more detail.

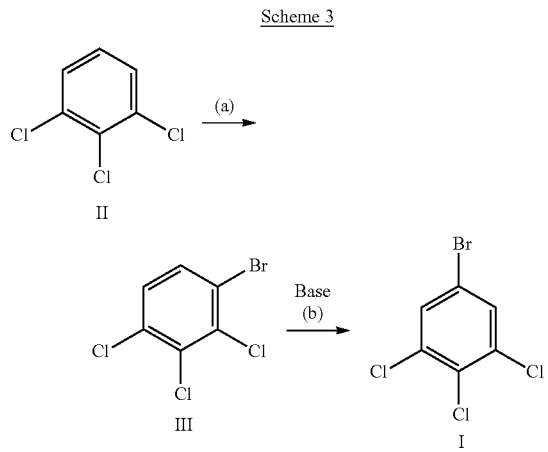

Scheme 3

Step a)

The compound of formula III can be prepared by reacting a compound of formula II with an electrophilic brominating agent. Suitable reagents include, but are not limited to bromine and N-bromo succinimide.

Typically the reaction is performed in the presence of a suitable acidic catalyst. Suitable catalysts include but are not limited to mineral acids such as sulfuric acid, hydrochloric acid and phosphoric acid and Lewis acids such as iron (Ill) bromide, aluminum bromide, boron trifluoride etherate and titanium tetrachloride. Optionally the desired catalyst can also be made in situ by mixing bromine with iron powder.

Transformation of the compound of formula II to the compound of formula III can be carried out without an organic solvent. Alternatively, solvents such as tetrachloromethane, 1,2-dichloroethane and carbon disulfide can be employed.

The reaction can be carried out at a temperature from 0° C. to 150° C., preferably from 40° C. to 120° C., most preferable from 60° C. to 100° C.

Step b)

The compound of formula I can be prepared from a compound of formula III by treatment with potassium tert-butoxide. This base may be used in both catalytic and stoichiometric quantities. The preferred amount is between 0.1 and 0.5 molar equivalents.

The reaction is preferably carried out in the presence of a solvent. The preferred solvents are tetrahydrofuran and 2-methyl-tetrahydrofuran, preferably tetrahydrofuran.

The reaction can be carried out at a temperature from −80° C. to 100° C., preferably from 0° C. to 50° C., most preferably at ambient temperature.

A preferred embodiment of the invention provides a process for the preparation of a compound of formula I

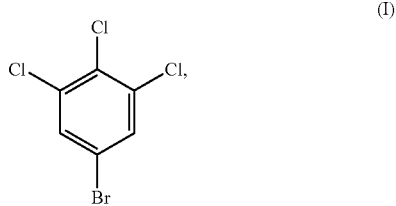

comprising a) reacting a compound of formula II

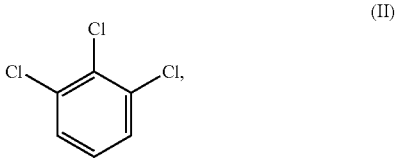

with a brominating agent selected from bromine and N-bromo succinimide in the presence of an acidic catalyst selected from the group consisting of sulfuric acid, hydrochloric acid, phosphoric acid and Lewis acids or prepared in situ by mixing bromine with iron powder, to form a compound of formula III,

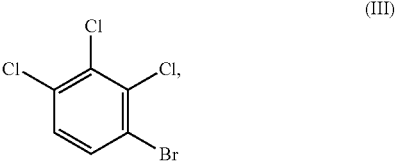

and b) reacting the compound of formula III in tetrahydrofuran with potassium tert-butoxide.

PREPARATORY EXAMPLES

Example 1: Preparation of 1-bromo-2,3,4-trichloro-benzene of formula III

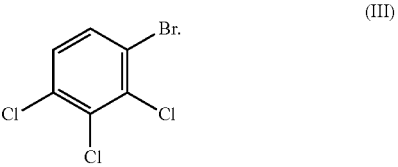

To a solution of 1,2,3-trichlorobenzene (1.5 g, 8.3 mmol) in tetrachloromethane (21 ml) was added iron powder (0.92 g, 17 mmol). To this suspension was added bromine (2.7 g, 17 mmol) and the resulting mixture was heated at 100° C. for 18 hours. The reaction was quenched by addition of a mixture of a saturated aqueous NaHCO$_3$ and 1M Na$_2$S$_2$O$_3$. The resulting mixture was filtered through celite, layers were separated and aqueous phase was extracted with dichloromethane (2×). The combined organic layers were dried over Na$_2$SO$_4$ and evaporated under reduced pressure. The crude product was purified by silica gel chromatography (eluting with pure heptane) to afford 1-bromo-2,3,4-trichloro-benzene (1.68 g) as a white powder.

$^1$H NMR (400 MHz, CDCl$_3$) δ 7.50 (d, J=8.8 Hz, 1H), 7.27 (d, J=8.8 Hz, 1H).

Alternatively, the compound of formula III can be also obtained by carrying out the following procedure:

1,2,3-trichloro-benzene was heated to 60° C. and iron (III) bromide (1.66 g, 5.5 mmol) was added followed by bromine (1.77 g, 11 mmol). The reaction mixture was stirred at 60° C. for 3 hours, cooled to ambient temperature, diluted with dichloromethane and quenched by pouring into a mixture of a saturated aqueous NaHCO$_3$ and 1M Na$_2$S$_2$O$_3$. The resulting mixture was filtered through celite, layers were separated and the aqueous phase was extracted with dichloromethane (2×). The combined organic layers were dried over Na$_2$SO$_4$ and evaporated under reduced pressure to afford pure 1-bromo-2,3,4-trichloro-benzene (2.81 g) as a beige powder.

Example 2: Preparation of
5-bromo-1,2,3-trichloro-benzene of formula I

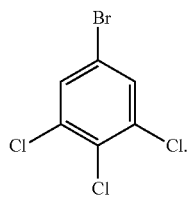
(I)

To a solution of 1-bromo-2,3,4-trichloro-benzene (50.0 g, 192 mmol) in dry tetrahydrofuran (25 ml) was added 1.0M KOtBu in THF (52 g, 58 mmol) and the resulting solution was stirred at ambient temperature for 1 hour. The reaction was acidified with aqueous HCl and the aqueous phase was extracted with dichloromethane (2×). The combined organic layers were dried over Na$_2$SO$_4$ and evaporated under reduced pressure. The obtained crude product (49.5 g) contains a mixture of 5-bromo-1,2,3-trichloro-benzene and 1-bromo-2,3,4-trichloro-benzene in a ratio 5.1:1. Both substances can be separated by distillation under reduced pressure and 1-bromo-2,3,4-trichloro-benzene can then be recycled.

$^1$H NMR (400 MHz, CDCl$_3$) δ 7.55 (s, 2H).

The invention claimed is:

1. A process for the preparation of a compound of formula I

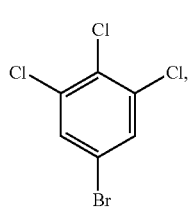
(I)

comprising
a) reacting a compound of formula II

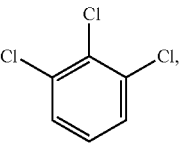
(II)

with a brominating agent in the presence of an acidic catalyst to a compound of formula III,

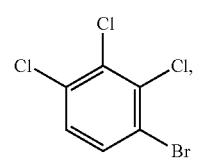
(III)

and, wherein the acidic catalyst is sulfuric acid, hydrochloric acid, phosphoric acid, Lewis acids or acidic catalyst prepared in situ by mixing bromine with iron powder; and wherein the brominating agent is bromine or N-bromo succinimide;

b) reacting the compound of formula III in tetrahydrofuran or 2-methyl-tetrahydrofuran with potassium tert-butoxide to form a compound of formula I.

2. A process according to claim 1, wherein the Lewis acid is iron (III) bromide, aluminum bromide, boron trifluoride etherate or titanium tetrachloride.

3. A process according to claim 1, wherein the compound of formula III is reacted in tetrahydrofuran with potassium tert-butoxide to form a compound of formula I.

4. A process according to claim 1 comprising
a) reacting a compound of formula II

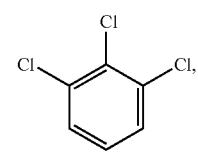
(II)

with a brominating agent selected from the group consisting of bromine and N-bromo succinimide in the presence of an acidic catalyst selected from the group consisting of sulfuric acid, hydrochloric acid, phosphoric acid, Lewis acids and acidic catalyst prepared in situ by mixing bromine with iron powder, to form a compound of formula III,

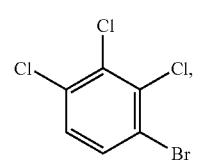
(III)

and
b) reacting the compound of formula III in tetrahydrofuran with potassium tert-butoxide to form a compound of formula I.

* * * * *